United States Patent [19]

Tajika

[11] 4,090,502
[45] May 23, 1978

[54] REMOTE-CONTROLLED BARIUM INJECTION APPARATUS

[75] Inventor: Akeo Tajika, Osaka, Japan

[73] Assignee: Medical Institute of Hoshokai, Osaka, Japan

[21] Appl. No.: 684,740

[22] Filed: May 10, 1976

[30] Foreign Application Priority Data

Aug. 22, 1975 Japan .................................. 50-102371

[51] Int. Cl.² .......................................... A61B 6/02
[52] U.S. Cl. .................................. 128/2 A; 128/241; 128/DIG. 12; 128/DIG. 13
[58] Field of Search .............. 128/2 A, 2 R, 230, 240, 128/241, DIG. 1, DIG. 12, DIG. 13

[56] References Cited

U.S. PATENT DOCUMENTS

| | | | |
|---|---|---|---|
| 2,564,809 | 8/1951 | Levene | 128/2 A X |
| 3,459,175 | 8/1969 | Miller | 128/2 A |
| 3,470,869 | 10/1969 | Fenton et al. | 128/2 A |
| 3,545,438 | 12/1970 | Devries | 128/230 UX |
| 3,701,345 | 10/1972 | Heilman et al. | 128/2 R X |
| 3,769,962 | 11/1973 | McVey | 128/2 A |
| 3,812,855 | 5/1974 | Banko | 128/2 A X |
| 3,888,239 | 6/1975 | Rubinstein | 128/2 A |

*Primary Examiner*—Kyle L. Howell
*Attorney, Agent, or Firm*—Wenderoth, Lind & Ponack

[57] ABSTRACT

Injection of barium into the lower digestive tract of a patient to be examined and subsequent reflux and evacuation of the barium by air compression is effected by remote control whereby greater safety is achieved in production of double contrast studies or fluoroscopic examination. The apparatus employs detachable anal insertion units which are the only portion of the apparatus in direct contact with a patient. A new anal insertion unit is used for each patient, whereby cleaning of the apparatus is made easier and hygiene is improved.

5 Claims, 6 Drawing Figures

REMOTE-CONTROLLED BARIUM INJECTION APPARATUS

BACKGROUND OF THE INVENTION

The present invention relates to an apparatus for injection of barium into the lower digestive tracts of the intestine of a patient concerning whom it is required to make a double contrast study. More particularly the invention relates to a barium injection apparatus by which barium is introduced into a patient via the anus of the patient and is caused to move by pressure into the intestinal canals of the patient, and air is subsequently introduced in a similar manner to expel the barium, and which permits remote control of the barium injection process.

It is known that examination and diagnosis of a patient suffering from intestinal disorder such as cancer of the intestine, intestinal ulcer, or enteritis, for example, is greatly assisted by production of a double contrast study, that is a radiographic picture taken while the patient's digestive tracts are lightly coated with barium and slightly expanded by air. However, although such a radiographic process in known to be advantageous it is employed only to a comparatively small degree. A first reason for this is that while examination of the oesophagous and the stomach or other upper digestive organs can be effected by using X ray or similar radiographic equipment to follow the course of barium which a patient drinks, conventionally, introduction of barium into the lower digestive organs has been found to be difficult, and also time-consuming. Another problem is that of repeated exposure of medical staff who are required to be present to supervise at least the drinking of barium by patients. A further problem is that a patient may object to drinking the barium. It has therefore been a strong desideratum in medical circles that there be provided means for barium injection which is safe and permits the entire process of production of double contrast studies to be mechanized and completed in a shorter time.

SUMMARY OF THE INVENTION

It is accordingly a main object of the invention to provide a barium injection apparatus which permits the entire process of double contrast study production to be remote-controlled whereby safety is improved.

It is a further object of the invention to provide a barium injection apparatus which requires no action of a patient, whereby production of a double contrast study may be effected quickly and easily.

In accomplishing these and other objects there is provided according to the present invention a remote-controlled barium injection apparatus which includes a separate air supply means and barium supply means which both connect to an anal insertion unit which is detachably connected to the main portion of the apparatus, which is insertable into the anus of a patient to be examined, and via which air and barium may be independently injected into or evacuated from the lower digestive organs of the patient, the insertion unit defining separate ducts and inlet and outlet ports for air and for barium. After insertion of the anal insertion unit all subsequent actuation of the apparatus may be controlled from a control panel provided in a room which is separated from that in which the patient is present. First, barium is supplied under pressure into the intestine of the patient, and then, air is supplied into the patient's intestine to cause reflux of the injected barium which is subsequently again drawn through the anal insertion unit and supplied into a suitable reception tank, the patient's lower intestine still being coated with a suitable amount of barium to permit production of a required radiograph. The position of the port for air in the anal insertion unit is such that when the insertion unit is in place in the anus of the patient the air port is above the remnant liquid in the rectum, whereas the position of the barium port is below the level of this liquid, whereby refluxed barium is efficiently directed to the barium port. While the main portion of the apparatus may be used for a plurality of patients the anal insertion unit is used for one patient only, a new insertion unit being attached to and subsequently detached from the apparatus for each patient examined. Since barium is not required to move through the digestive organs of a patient under the effect of gravity but is injected under pressure, the patient may be radiographically examined while lying down thereby avoiding problems of undesirable movement such as is liable to occur when a patient must stand for the entirety of the examination. The apparatus is provided with flow control and safety valve means ensuring that the quantity of feed of and pressure of barium and air in the patient's intestine are kept within requisite values, and the control panel is provided with visual displays indicating the amount of barium and of air supplied. Thus all stages of the examination may be controlled, and easily conducted in conditions of safety both for patients examined and for medical staff responsible for the examination.

BRIEF DESCRIPTION OF THE DRAWINGS

A better understanding of the present invention may be had from the following full description thereof when read in reference to the attached drawings, in which like numbers refer to like parts, wherein

FIG. 2a is a longitudinal cross-sectional view showing details of construction of an anal insertion unit;

FIG. 2b is a cross-sectional view taken along the line A—A of FIG. 2a;

DETAILED DESCRIPTION OF THE INVENTION

Figure 1:
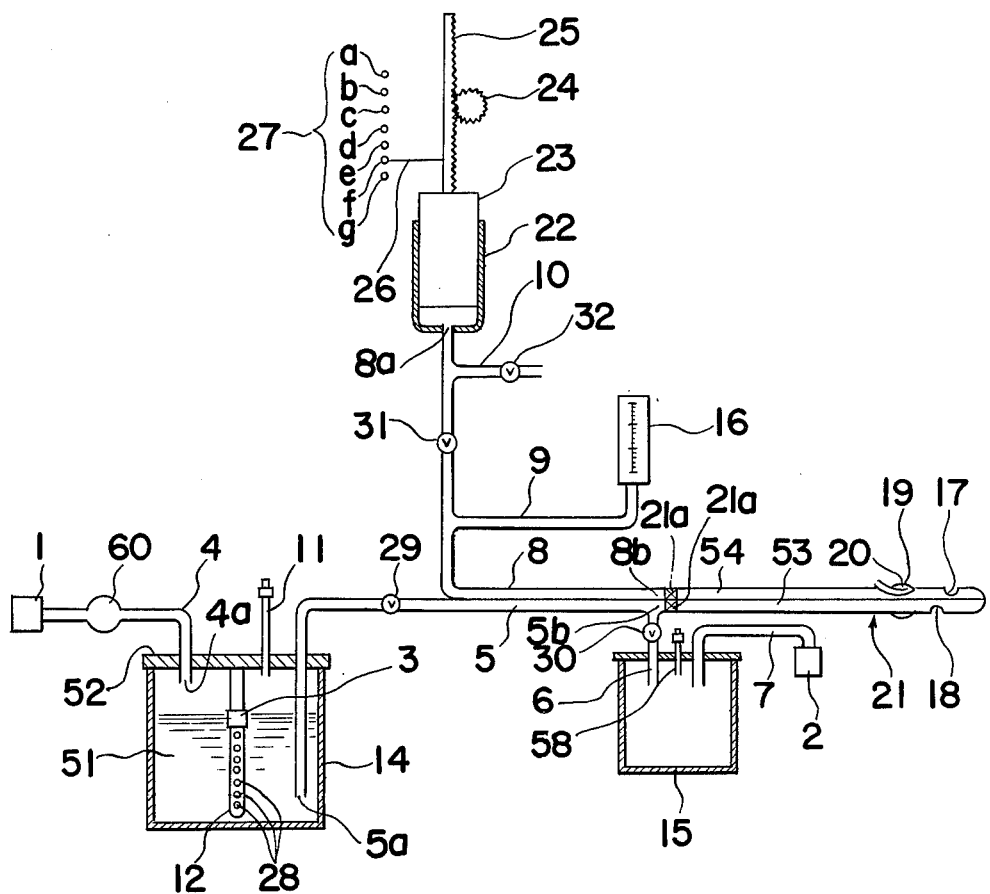
FIG. 1 is a side elevation showing the general layout of a remote-controlled barium injection apparatus according to the invention.

Referring to FIG. 1, the apparatus according to the invention comprises a compressor unit 1 which connects to an air reservoir 60, as shown schematically in the leftmost portion of the drawing. Upon actuation of the compressor unit 1 air from the reservoir 60 is supplied via a compressed air duct 4 into a tank 14, which contains an initial supply of barium 51 in liquid form and which is hermetically sealed by a cover 52, the compressed air duct 4 fitting exactly in an opening formed in the cover 52, and extending into the upper portion of the tank 14 to a distance such that the outlet opening 4a thereof is always above the level of the barium 51, even when the amount of barium 51 is maximum. Also fitting exactly in the cover 52 there is a barium supply duct 5 which extends downwards into the tank 14 a distance such that the intake opening 5a thereof is always below the level of the barium 51, even when the amount of barium 51 is minimum, barium 51 being withdrawable from the tank 14 via the supply duct 5, the level of barium 51 of course falling during this withdrawal from an initial highest level to a subsequent lowest level.

In the cover 52 there is also fitted a safety valve 11 which opens to the atmosphere when air pressure above the barium 51 in the tank 14 reaches a certain set value. Fixed to the lower surface of the cover 52 there is a downwardly extending vertical rod 12 which extends into the lowermost portion of the tank 14. On that portion of the rod 12 which lies between the highest level and lowest level of barium 51 in the tank 14 there is provided a series of switches 28 which are disposed in vertical succession to one another. A freely slidable float 3 is mounted on or around the vertical rod 12, and always floats on the surface of the barium 51. As the level of the barium 51 in the tank 14 falls due to withdrawal via the supply duct 5 the float 3 moves downwards and successively actuates the switches 28. Once actuated each switch 28 remains actuated until the next switch 28 is actuated. The switches 28 connect to a circuit which is provided in a control panel 56, described in greater detail later, and which produces a display which is varied in accordance with which of the switches 28 is currently actuated, whereby a medical attendant may know how much barium 51 has been withdrawn from the tank 14.

The barium supply duct 5 extends in a generally horizontal line from the barium supply tank 14 and the opposite end 5b thereof is detachably connected by a flexible coupling element 21a to a barium injection and evacuation duct 53 which constitutes part of an anal insertion unit 21 and also connects to a barium exhaust duct 6 which connects to a point of the supply duct 5 between the duct end 5b and the tank 14. An electromagnetic control valve 29 is provided on the barium supply duct 5 between the tank 14 and the junction of the duct 5 and the duct 6. On the exhaust duct 6 there is provided an electromagnetic control valve 30.

The exhaust duct 6 leads vertically downwards into a tank 15 for reception of exhausted barium, i.e., removed from a patient. Negative pressure to draw exhaust barium into the reception tank 15 is created in the tank 15 by a suction unit 2 connected by a pipe 7 to the upper portion of the tank 15. The upper portion of the reception tank 15 connects to the atmosphere via a safety valve 58, which is normally closed and which opens when negative pressure in the tank 15 exceeds a certain value.

In addition to the barium injection and evacuation duct 53, the anal insertion unit 21 includes an air injection duct 54 and an inflatable retainer ring 19. The intake end of the air injection duct 54 is detachably connected by means of the flexible coupling element 21a to one end 8b of an air supply duct 8. Thanks to the connection by the flexible coupling element 21a, the anal insertion unit 21 as a whole may be moved to a vertical or horizontal alignment independently of the rest of the apparatus, while still remaining connected to the rest of the apparatus, which may be stationary.

The opposite end 8a of the air supply duct 8 communicates with the lower end of a cylinder 22 whose upper end is open. On the duct 8 there is provided an electromagnetic control valve 31. An atmosphere duct 10 on which there is provided an electromagnetic control valve 32 has one end connecting to the air supply duct 8 at a point of the duct 8 between the end 8a thereof and the control valve 31 provided thereon and an opposite end leading to the atmosphere. A branch line 9 connects to a point of the air supply duct 8 between the control valve 31 and the end 8b of the duct 8 and leads to a manometer 16 employing a mercury column 49 not shown in FIG. 1. The pressure indicated by the manometer 16 is therefore that present in the lower portion of the air supply duct 8 and air injection duct 54. As described in greater detail below, when this pressure exceeds a set value the mercury column 49 closes a circuit, which when closed causes an alarm to be given.

In the upper portion of FIG. 1, a vertically-aligned piston 23 is slidably accommodated in the abovementioned cylinder 22. The upper end of the piston 23 extends to above the upper, open end of the cylinder 22 and has fixedly attached thereto an upwardly extending rack element 25 to the untoothed portion of which is fixedly attached a horizontal rod 26, and the toothed portion of which is engaged by a rotatable pinion 24. The pinion 24 is drivable by a motor 57, not shown in FIG. 1, whereby the rack element 25 may be driven upwards and downwards to cause upward and downward sliding movement of the piston 23 in the cylinder 22, the piston 23 being driven upwards and sucking air from the duct 10 into the air supply duct 8 upon opening of the electromagnetic control valve when the pinion 24 is rotated clockwise, while the piston 23 is driven downwards and forcing air from the one end 8a to the other end 8b of the air supply duct 8 upon closing of the electromagnetic control valve when the pinion 24 is rotated anti-clockwise as seen in the drawing. During such movement of the rack element 25 the outer end of the rod 26 attached thereto may successively actuate each one of a series of switches 27a through 27g in a switch bank 27. Switch 27a only is a normally closed switch, switches 27b through 27g being normally open switches. Normally, i.e., during non-actuation of the apparatus, the cylinder 23 is in an uppermost position and the rod 26 contacts and actuates switch 27a. When the piston 23 reaches the lowermost point of a downward stroke, the rod 26 actuates switch 27g.

Figure 2:
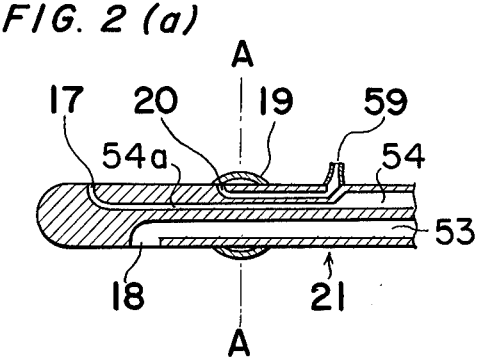
Figure 2:
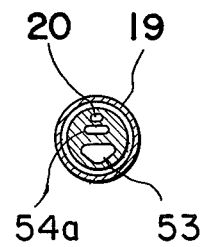

Still referring to FIG. 1 and also referring to FIGS. 2a and 2b, the anal insertion unit 21 which is the portion of the apparatus which is actually inserted into the anus of a patient has the general shape of a round rod. In a forward end portion of the insertion unit 21 there is defined a small air port 17 which communicates with a small-bore leading end portion 54a of the air injection duct 54. On the opposite side of the insertion unit 21 there is defined a barium injection and evacuation port 18 which communicates with the barium injection and evacuation duct 53, and is further removed than the air injection port 17 from the forward end of the insertion unit 21. As shown most clearly in FIGS. 2a and 2b, the leading end portion 54a of the air injection duct 54 has a generally elliptic cross-section and defines a much smaller bore than the barium injection and evacuation duct 53. Around a portion of the insertion unit 21 which is further removed from the forward end thereof than the barium injection and evacuation port 18 there is provided the inflatable ring element 19, which has opposite edge portions fixed to the insertion unit 21 and whose interior communicates with an air passage 20 defined in the insertion unit 21 and leading rearwards, i.e., away from the forward end of the unit 21, to a pump port 59 fitted with a suitable valve or sealing means. After insertion of the unit 21 into the anus of a patient, a small amount of air is injected, by means of a hand pump, air injector or other suitable means, through the air passage 20 to inflate the ring element 19, after which the port 59 is sealed, whereby the inflated ring element 19 prevents the insertion unit 21 from falling naturally from the anus of the patient.

Figure 3:
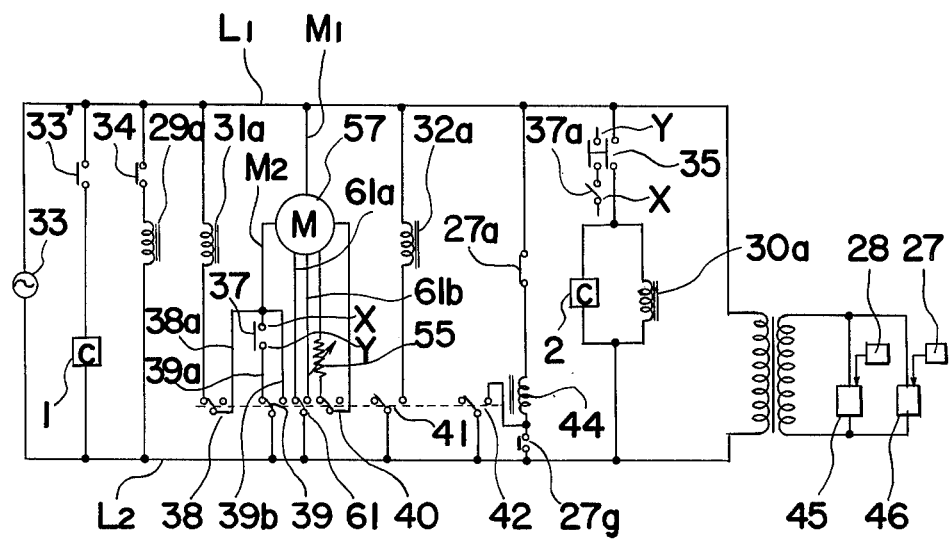
FIGS. 3a and 3b are block diagrams of electrical control circuit means for the apparatus of FIG. 1.
FIG. 3c is a schematic view showing the layout of a control panel for the apparatus of FIG. 1.
Figure 3:
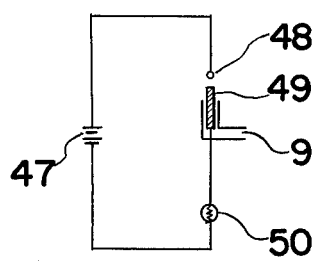
Figure 3:
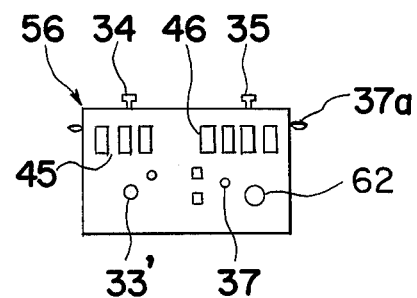

Reference is now had to FIGS. 3a and 3b which show the electrical control circuit of the above described means. Power to the circuit is supplied from an alternating current source 33 across power lines L1 and L2. The abovementioned motor 57 connects to line L1 through a line M1 and may connect to line L2 through a line M2 and through a line 61a or 61b which are selectively connectable to line L2 by a switch 61.

The line M2 connects to independent lines 38a, 39a and 39b. The lines 39a and 39b are selectively connectable to line L2 by a switch 39 which is normally closed on line 39a. On line 39a there is provided a pair of terminals X and Y which are normally open but which may be connected by closure of an externally actuable push-button switch 37. The switch 37 is a non-lock type whereby connection of terminals X and Y is maintained only while the push-button switch 37 is held depressed. The line 38a connects through a normally closed switch 38 to the lower end of an electromagnetic element 31a which is in parallel to the motor 57 and has an upper end connecting to the line L1, and which controls the abovementioned valve 31 on the air supply duct 8. Thus, the electromagnetic element 31a is energized when push-button switch 37 is depressed and switches 38 and 39 are in their normal positions.

The abovementioned switch 61 is normally closed on line 61a, and in this case closure of the power supply circuit of the motor 57 causes the motor 57 to be driven forwards, which is the direction for causing the piston 23 of FIG. 1 to move downwards and drive air into the air supply duct 8.

Still in FIG. 3a, the motor 57 has associated therewith a speed control circuit which includes a variable resistor 55 and which may be opened upon opening of a normally closed switch 40.

In the left portion of FIG. 3a, the compressor unit 1 and an externally actuable push-button switch 33' in series therewith are provided across the power lines L1 and L2 in parallel to the motor 57. An electromagnetic element 29a which controls the valve 29 on the barium supply duct 5 and is in series with an externally actuable push-button switch 34 is also provided across the lines L1 and L2 in parallel with the motor 57. The push-button switches 33' and 34 are both of a locking type and at the start of actuation are open. Each switch 33' and 34 is closed upon depression thereof, and remains closed until it is again depressed.

To the right of the motor 57 as seen in the drawing there is provided an electromagnetic element 32a which controls the valve 32 on the air intake line 10, which is in parallel with the motor 57, whose upper end connects directly to line L1 and whose lower end is connected to line L2 when a normally open switch 41 is closed.

The uppermost, normally closed switch 27a in the switch bank 27 which is actuable by the rod 26 attached to the piston drive rack 25 connects the line L1 to the upper end of an electromagnetic element 44 whose lower end may connect to the line L2 through the lowermost, normally closed switch 27g of the switch bank 27 and through a normally open, self-hold switch 42. The switches 38, 39, 61, 40, 41 and 42 are ganged.

The compressor unit 2 for creation of negative pressure in the exhaust barium reception tank 15 and an electromagnetic element 30a which controls the valve 30 on the exhaust duct 6 are provided in parallel to one another and to the motor 57 and have lower ends connecting directly the line L2 and upper ends connecting to the line L1 through a normally open switch 35. The switch 35 is ganged with a switch 35a, which, on condition that a normally open switch 37a is closed, closes the contacts X and Y on the line 39a of the power supply circuit of the motor 57 simultaneously with actuation of the switch 35.

In FIG. 3b the mercury column 49 in the abovementioned manometer 16 connecting through the branch line 9 to the air supply duct 8 is provided in an alarm circuit in series with a direct current source 47, an open contact terminal 48, and alarm buzzer 50, or indicator lamp or similar means, the mercury column 49 being physically immediately below the contact terminal 48 and the alarm circuit being normally open and being closed when pressure in the duct 8 is sufficient to cause the mercury column 49 to rise as far as the contact terminal 49.

In FIGS. 3a and 3c, power from the AC power supply 33 is supplied through suitable transformer means to actuate the circuits of digital display units 45 and 46 which are provided on a control panel 56. The circuits of the display units 45 and 46 respectively receive input from the set of switches 28 on the barium supply tank rod 12 and the switch bank 27 associated with the air supply piston 23, and effect A – D conversion of their respective inputs, the display unit 45 giving a digital indication of the amount of barium 51 which is supplied out of the supply tank 14 and the display unit 46 giving a digital indication of the amount of air supplied into the air supply duct 8 due to downward movement of the piston 23. The control panel 56 also has provided thereon the abovementioned push-button switches 33', 34, 35, and 37, normally open switch 37a, and an adjustment knob 62 which controls the position of the slider of the variable resistor 55 in the motor 57 speed control circuit. In the room in which the control panel 56 is located there is also suitably provided a monitor television screen on which the patient and room containing the barium injection apparatus may be viewed. In addition there may of course be provided intercommunication means permitting the medical attendant to communicate with the patient.

Utilization of the abovedescribed apparatus is as follows. First a patient to be examined lies down in a suitable position in a room in which the apparatus of FIG. 1 is provided. Next, the anal insertion unit 21 is inserted into the anus of the patient and air is injected via the port 59 to inflate the ring 19 sufficiently to retain the insertion unit 21 in position in the anus of the patient, this process being effected by a medical attendant.

When this is completed, the radiologist proceeds to another room in which the control panel 56 is provided and first presses push-button switch 33' to actuate the compressor 1, which now causes air to be supplied from the air reservoir 60 into the barium supply tank 14 and apply pressure on the surface of the barium 51. Next, the radiologist presses push-button switch 34, whereupon the electromagnetic element 29a opens valve 29 on the barium supply duct 5. Switch 35 being unactuated at this time valve 30 on the barium exhaust duct 6 is closed, and the air supplied into the tank 14 by the compressor 1 therefore causes barium 51 to be supplied along the supply duct 5 and barium injection and evacuation duct 53, through the port 18 and into the rectum of the patient. Even if there is variation in the efficiency of the compressor 1, the rate of this supply cannot exceed a certain maximum since the safety valve 11 in the supply tank cover 52 opens when air pressure in the supply tank 14 exceeds certain set value. During this supply, barium 51 in the tank 14 gradually falls and the float 3 therefore actuates successively lower switches in the set of switches 28 on the rod 12, resulting in a digital display on the display unit 45 indicating to the radiologist the amount of barium which has been supplied into the rectum of the patient, the circuit associated with the display unit 45 of course including a suitable subtraction circuit to take into account the amount of barium which is present in the barium supply duct 5 and injection and evacuation duct 53.

Upon ascertaining by observation of the display unit 45 that a requisite amount of barium has been supplied into the rectum of the patient, the radiologist again actuates push-button switches 33' and 34 whereby actuation of the compressor unit 1 is stopped, valve 29 is closed and supply of barium ceases.

Next, the radiologist closes push-button switch 37 thereby actuating motor 57 and energizing electromagnetic element 31a to open the valve 31 on the air supply duct 8. At this time, the motor drive changeover switch 61 is closed on line 61a and the motor 57 therefore supplies forward drive to the piston 23, and also the switch 41 is open and the control valve 32 on the atmosphere line 10 is therefore closed. The piston 23 is now moved downwards and causes air to be supplied along the air supply duct 8 and injection duct 54 and through the port 17, so causing the previously injected barium to be refluxed from the rectum to the colon of the patient. Since, as noted earlier, the air injection port 17 is further forward than the barium injection and evacuation port 18, the refluxed barium does not block the air port 17, but is moved to a lower portion of the patient's rectum. While air is thus supplied, the rod 26 attached to the rack 25 actuates successively lower switches in the switch bank 27, whereby a digital display indicating the amount of air supplied is given on the display unit 46, this display taking into account the amount of air present in the supply duct 8 and injection duct 54. While observing the display of display unit 46, the radiologist adjusts the setting of the slider of the variable resistor 55 by means of the control knob 62 and also actuates push-button 37 in a suitable manner, in order to bring the speed of the motor 57 to value such that air is not supplied at a rate liable to cause discomfort to the patient. In addition an independent indication of air pressure in the supply line 8, and hence of air pressure in the rectum of the patient, is given by the manometer 16, and if this pressure reaches a value which approaches an undesirably high value the alarm circuit shown in FIG. 3b is closed and the buzzer 50 is actuated to give a warning to the radiologist who may therefore take suitable action such as stopping actuation of the motor 57.

As soon as the rack 25 starts to move downwards the rod 26 attached thereto is moved out of contact with the uppermost, normally closed switch 27a of the switch bank 27, and the switch 27a therefore closes. Despite closure of switch 27a, the electromagnetic element 44 is not yet actuated, since at this time switch 42 is open and the rod 26 has not yet reached the lowermost, normally open switch 27g of the switch bank 27. When however a requisite amount of air has been supplied through the anal insertion unit 21, switch 27g is actuated by the rod 26, thereby closing the power supply circuit to electromagnetic element 44, which now causes the self-hold switch 42 to close and the switches 38, 39, 61, 40 and 41 ganged with switch 42 to move to the right as seen in FIG. 3a, i.e. switches 38 and 40 open, switches 39 and 61 move to contact lines 39b and 61b respectively and switch 41 closes the power supply circuit to electromagnetic element 32a. At this time the radiologist completely releases the push-button switch 37 thereby opening the terminals X and Y on the line 39a.

Switch 38 now being open electromagnetic element 31a is de-energized and valve 31 on the air supply duct 8 is closed, while at the same time electromagnetic element 32a is energized and opens valve 32 on the duct 10 leading to the atmosphere. Although line 39a is open, the power supply circuit to the motor 57 is still closed by lines M1, M2 and 39b and switch 39, but since switch 61 is now closed on line 61b the motor 57 is driven in reverse, whereby the pinion 24 is driven clockwise as seen in FIG. 1, the rack 25 and piston 23 are driven upwards, and air is drawn into the cylinder 22 via the atmosphere duct 10 and the upper portion of the air supply duct 8. During this reverse drive of the motor 57 there is no need for motor speed control since valve 31 being closed there is no effect on the patient, and the variable resistor 55 may therefore be disconnected from the motor 57 control circuit by opening of switch 40.

As soon as the piston 23 and rack 25 start to move upwards, the rod 26 moves out of contact with the lowermost switch 27g, which therefore opens. However, the power supply circuit to electromagnetic element 44 is still closed by switch 27a and switch 42 and switches 38, 39, and 40 through 42 therefore remain in their switched condition and motor 57 continues to be driven in reverse. These conditions are maintained until the rod 26 again reaches and actuates the uppermost switch 27a of the switch bank 27a, at which time switch 27a is opened, resulting in de-energization of electromagnetic element 44. The switches 38, 39, 61, 40, 41, and 42 therefore all move leftwards back to their unactuated positions, conditions thus becoming as at the start of actuation of the apparatus, i.e., all control valves 29 through 32 are closed, motor 57 although unactuated, since switch 39 is closed on line 39a and push-button switch 37 is unactuated, is ready to be actuated in forward drive since switch 61 is closed on the line 61a, and the motor speed control circuit is closed by switch 40.

Irrespective of rate of flow of air supplied from the cylinder 22, the total amount of air supplied between the time the rod 26 on the rack 25 moves from the uppermost switch 27a to the lowermost switch 27g of the switch bank 27 of course depends on the internal diameter of the piston and the distance between the switches 27a and 27g. The same circuit action as described above may be effected for different total amounts of air supply by provision of a plurality of switch banks 27 in each of which the distance from the uppermost switch 27a to 27g is different, and which are interchangeable in a known manner. In such a case it is preferable that relative to the cylinder 22 the position of the lowermost switch 27g of any switch bank 27 mounted in position for contact by the rod 26 be the same in all switch banks 27, and that the distance of the uppermost switch 27a above the lowermost switch 27g be varied in different switch banks 27.

Next, the patient stands up, this movement being permitted by the flexible coupling 21a connecting the main portion of the apparatus and the anal insertion unit 21, whereupon excess barium falls under gravity into the lower anal region of the patient. The radiologist now actuates switch 35, so causing energization of the electromagnetic valve 30a to open the valve 30 on the barium exhaust line 6 and actuation of the compressor 2, which creates in the barium reception tank 15 a negative pressure which causes barium to be drawn through the injection and evacuation port 18, along the injection and evacuation duct 53 and exhaust duct 6, and into the reception tank 15, barium in the forward part of the barium supply duct 5, i.e., the supply duct 5 portion to the right of the currently closed valve 29 as seen in FIG. 1, also being drained into the reception tank 15. Application of excessive suction pressure on the mucous membrane of the rectum of the patient during this evacuation of the barium is avoided since the safety valve 58 opens to the atmosphere if negative pressure in the reception tank 15 reaches a certain set value, as noted earlier.

Since evacuation of the barium from the intestine of the patient may result in contraction of the intestinal walls of the patient, the radiologist may consider it preferable to resupply air simultaneously into the intestine of the patient to counter this contraction. In this case, before actuating switch 35, the radiologist sets the variable resistor control knob 62 to the position for causing lowest speed of the motor 57 and also actuates switch 37a, whereby, simultaneously with subsequent closure of switch 35, switch 35a completes contact between terminals X and Y on line 39a. Valve 31 is therefore again opened, motor 57 is actuated in forward drive, and air is again supplied into the intestine of the patient, as the level of barium being evacuated gradually lowers to below the level of the air injection port 17, this air acting to re-inflate and avoiding contraction of the intestine of the patient and so permitting obtaining of a good double contrast view. The second supply of air may be stopped while barium is still being evacuated by switching off the switch 37a. When the excess barium has been evacuated, radiologist may enter the room in which the patient is present to discharge air from the flexible retainer ring 19 and remove the anal insertion unit 21, after which taking X-ray photograph or a fluoroscopic examination can be continued. Subsequent removal of barium coating the patient's intestine may be effected in a known manner, by administration of a purge, for example.

The anal insertion unit 21 is discarded subsequent to use thereof, and a new insertion unit 21 used for each patient examined thereby ensuring conditions of good hygiene and also permitting the apparatus to be rapidly made available for successive patients.

Thus the invention provides a barium injection apparatus having the following advantages.

1. Since a radiologist is required to be present in a examining room only for insertion and removal of the anal insertion unit 21, and during all other time such as barium injection and evacuation stages he can stay in a separate room being completely protected from X-ray exposure problems of repeated exposure are completely resolved.

2. Since very little action is required of the patient to have injected barium proceed effectively in a desired way into the lower digestive tract of the patient, the radiologist succeeds always in obtaining good blur-free radiographic pictures with efficient coating.

3. Being automated the process as a whole may be effected rapidly and so double contrast studies for early detection of disorders in the lower digestive tract or for examination and diagnosis for sufferers from such disorders may be used much more commonly than has been possible higherto.

4. From the point of view of the patient, hygienic conditions are maintained by use of replaceable anal insertion units 21, and safety is ensured by provision of requisite safety valves as well as display means to assist the radiologist.

What is claimed is:

1. A remote-controlled barium injection apparatus comprising:
   an anal insertion unit insertable in the anus of a patient, said anal insertion unit having in a leading end portion thereof an air injection port and a separate barium injection and evacuation port;
   barium supply system means, connectable to said barium injection and evacuation port, for supplying barium under pressure to said barium injection and evacuation port and therethrough into the intestine and rectal region of a patient;
   air supply system means, connectable to said air injection port, for supplying air under pressure to said air injection port and therethrough into the intestine and rectal region of a patient;
   barium exhaust system means, connectable to said barium injection and evacuation port, for evacuating barium from the intestine and rectal region of a patient through said barium injection and evacuation port;
   first measurement means, operatively connected to said barium supply system means, for measuring the amount of barium supplied by said barium supply system means to said barium injection and evacuation port;
   second measurement means, operatively connected to said air supply system means, for measuring the amount of air supplied by said air supply system means to said air injection port; and
   a control panel separately located from the remainder of the apparatus and including:
   barium supply actuation means, remotely connected to said barium supply system means, for actuating said barium supply system means and for supplying barium therefrom through said barium injection and evacuation port of said anal insertion unit into the intestine and rectal region of a patient;
   first display means, remotely connected to said first measurement means, for displaying values measured by said first measurement means;
   air supply actuation means, remotely connected to said air supply system means, for actuating said air supply system means and for supplying air therefrom through said air injection port of said anal insertion unit into and causing inflation of the intestine and rectal region of the patient;
   second display means, remotely connected to said second measurement means, for displaying values measured by said second measurement means; and
   barium exhaust actuation means, connected to said air supply actuation means and remotely connected to said barium exhaust system means, for actuating said barium exhaust system means and for removing excess barium from the intestine and rectal region of the patient through said barium injection and evacuation port of said anal insertion unit, while again actuating said air supply actuation means and thereby maintaining inflation of the intestine and rectal region of the patient.

2. An apparatus as claimed in claim 1, wherein said anal insertion unit is removably attached to said air supply system means, said barium supply system means and said barium exhaust system means, wherein said anal insertion unit further includes selectively operable retention means for preventing undesired removal of said anal insertion unit from the anus of a patient, and wherein said air injection port is located closer to the leading end of said anal insertion unit than said barium injection and evacuation port.

3. An apparatus as claimed in claim 2, wherein said retention means comprises an inflatable ring member positioned externally around said anal insertion unit.

4. An apparatus as claimed in claim 1, wherein said air supply system means comprises a cylinder connectable to said air injection port, and piston means movable within said cylinder for moving air therethrough, and said second measurement means comprises a bank of switches positioned in a line parallel with the direction of movement of said piston means within said cylinder, and switch actuator means mounted on said piston means and movable therewith for successively actuating said switches during movement of said piston means.

5. An apparatus as claimed in claim 1, wherein said barium supply system means comprises a storage tank for storing therein an initial supply of barium, said storage tank being connectable to said barium injection and evacuation port, and said first measurement means comprises a vertical rod fixedly positioned within said storage tank, a plurality of switches vertically spaced along said rod, and float means, positioned about said rod and vertically movable therealong in response to the level of barium in said storage tank, for successively actuating said switches during movement of said float means.

* * * * *